US 6,719,708 B1

(12) United States Patent
Jansen

(10) Patent No.: US 6,719,708 B1
(45) Date of Patent: Apr. 13, 2004

(54) DEVICE AND METHOD FOR MEASURING VALUES FROM A PERSON LYING DOWN, AND PRESSURE SENSOR

(75) Inventor: Klaus Jansen, Buxtehude (DE)

(73) Assignee: Thomas Hilfen Hilbeg GmbH & Co. Kommanditgesellschaft, Bremervorde (DE)

( * ) Notice: Subject to any disclaimer, the term of this patent is extended or adjusted under 35 U.S.C. 154(b) by 19 days.

(21) Appl. No.: 09/685,429

(22) Filed: Oct. 10, 2000

(30) Foreign Application Priority Data

Oct. 19, 1999 (DE) .......................... 199 50 291
Jan. 18, 2000 (DE) .......................... 100 01 698

(51) Int. Cl.⁷ .......................... A61B 5/103; A61B 5/117
(52) U.S. Cl. .................................... 600/587
(58) Field of Search ................. 600/587, 595, 600/300; 340/572.1, 573.1, 664, 665, 666, 825.36, 573.4, 575, 667; 307/10.1; 180/273

(56) References Cited

U.S. PATENT DOCUMENTS

| | | | |
|---|---|---|---|
| 2,644,332 A | | 7/1953 | Ulrich |
| 4,175,263 A | * | 11/1979 | Triplett et al. ........... 340/573.4 |
| 5,479,939 A | | 1/1996 | Ogino |
| 6,208,250 B1 | * | 3/2001 | Dixon et al. ............. 340/572.1 |
| 6,259,167 B1 | * | 7/2001 | Norton ..................... 307/10.1 |

FOREIGN PATENT DOCUMENTS

| | | |
|---|---|---|
| DE | 23 45 551 A | 9/1973 |
| DE | 28 52 351 C2 | 9/1980 |
| DE | 30 49 347 A1 | 7/1982 |
| DE | 31 33 026 A1 | 3/1983 |
| DE | 86 01 150 U1 | 4/1986 |
| DE | 36 17 012 A1 | 11/1986 |
| DE | 37 09 533 C2 | 12/1988 |
| DE | 30 09 216 C2 | 10/1989 |
| DE | 91 00 370 U | 6/1991 |
| DE | 42 40 782 A1 | 6/1994 |
| DE | 197 55 469 A1 | 6/1999 |
| EP | 0 671 145 A1 | 9/1995 |
| FR | 2 720 622 A | 12/1995 |
| GB | 2 329 250 A | 3/1999 |
| JP | 6-269427 A | 9/1994 |
| WO | WO 98/34577 A1 | 8/1998 |
| WO | WO 99 15 076 A1 | 4/1999 |

* cited by examiner

Primary Examiner—Max F. Hindenburg
Assistant Examiner—Brian Szmal
(74) Attorney, Agent, or Firm—Technoprop Colton LLC

(57) ABSTRACT

A device and method for measuring values from a person lying down and to a pressure sensor that can be used for this purpose. The invention improves the acquisition of measurement data in a mattress having sensors arranged in the region of the thorax and or sacrum by using a measurement method in which measured values from the sensors are measured and recorded continuously.

35 Claims, 4 Drawing Sheets

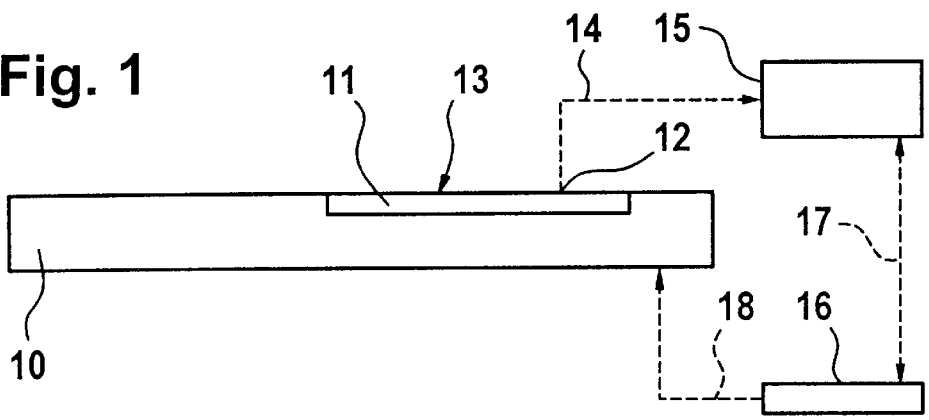
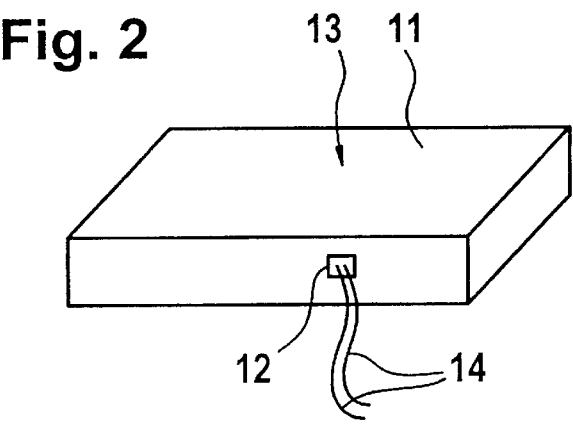
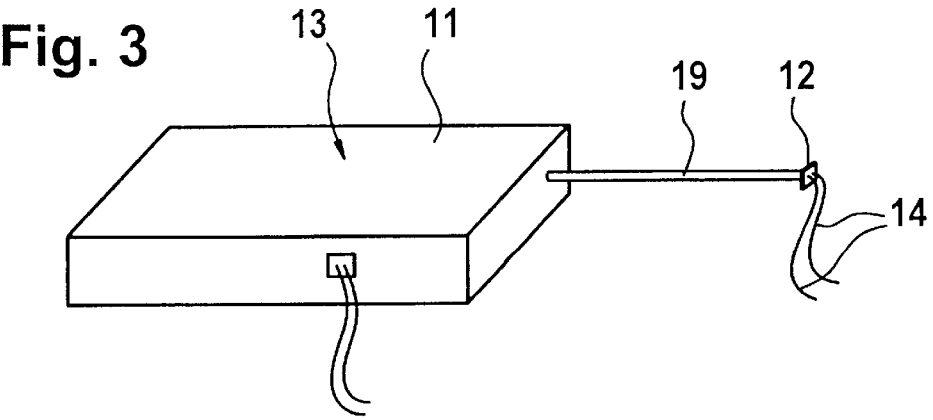

DEVICE AND METHOD FOR MEASURING VALUES FROM A PERSON LYING DOWN, AND PRESSURE SENSOR

BACKGROUND OF THE INVENTION

TECHNICAL FIELD

The invention relates to a device for measuring values from a person lying down, in particular the movement, direction of movement and/or vital parameters of this person, using sensors. The invention also relates to a method for measuring values of this nature. Finally, the invention relates to a pressure sensor having a sensor element.

It is known to measure pressure values of body parts of a person lying on a mattress. Measurements of this nature are used primarily to prevent decubitus. A device which is known from DE 42 40 782 A1 for this purpose has a multiplicity of sensors, namely 33 rows of in each case 23 sensors, making a total of more than 600 sensors, which measure the compressive loads and transmit measured values obtained to an evaluation unit.

This known device has the drawback of being susceptible to faults, on account of the large number of sensors. Furthermore, each individual sensor has to be calibrated, so that the measurement results from the individual sensors can be compared with one another. This requires a very high level of outlay, in particular since this calibration has to be repeated at specified maintenance intervals.

BRIEF SUMMARY OF THE INVENTION

The invention is therefore based on the technical problem of improving the measurement of values from a person lying down.

To solve this problem, a device of the type described in the introduction is characterized in that sensors are arranged in the region of the thorax and/or the sacrum. Furthermore, the problem is solved by a method for measuring values from a person who is on a device of this nature, in which measured values from the sensors in the region of the thorax and/or the sacrum are measured and recorded continuously.

According to the invention, the sensors are arranged in that area of the device in which the chest of a person lying on the mattress is situated—the area known as the thorax—and/or in the area in which the abdomen of the person is situated, the region known as the sacrum. As a result, the sensors are situated in the region of the centre of gravity of a person lying on the mattress. This advantageously enables movements and the direction of these movements by the person to be detected. Furthermore, arranging a sensor in the region of the thorax also advantageously enables the heartbeat and the respiration of the person to be detected.

It is preferable for pressures to be measured using a sensor cushion and to be evaluated in an evaluation unit, in that absolute pressures from the sensor cushions and/or relative pressures between a plurality of sensor cushions are combined in a calculation, in order to determine a movement, the direction of this movement and/or vital parameters of the person.

A pressure sensor according to the invention is characterized in that the pressure sensor has a sensor cushion which is filled with a gaseous or liquid medium, it being possible for a pressure which can be exerted on the sensor cushion to be transmitted via the medium to the sensor element. In this context, the term "pressure sensor" is to be understood as meaning a (relatively large) arrangement having a cushion—the sensor cushion—and at least one sensor element (which is relatively small in the context of this arrangement).

A pressure sensor according to the invention arranged in or on the device or mattress according to the invention offers the advantage of itself increasing the pick-up area and therefore the measurement range of a sensor element by a multiple compared to the pick-up area of the sensor element. For this purpose, the pressure element is connected to a cushion which is able to transmit a pressure exerted by a person who is on the mattress to the sensor element. Overall, the connected sensor cushion leads to an increase in the surface area of the sensor element. As a result, it is sufficient to equip a mattress with only a small number of, in particular two to four or five, pressure sensors, while nevertheless obtaining measurements which cover a large area of the mattress.

The cushion is preferably enclosed by a liquid-tight and/or airtight cover and is filled with a gaseous or liquid medium which transfers the pressure to the sensor element. This medium may in particular be air, water or a gel-like substance.

Preferably, the sensor cushion is also filled with an elastic material, for example foam. This is particularly advantageous in the case of an air-filled sensor cushion. This is because the filling with the elastic material means that the sensor cushion always returns to its optimum shape. This applies even if the inherently airtight cover has become air-permeable, for example as a result of slight damage, which would cause a cushion filled only with air to collapse. A pressure measurement using a sensor cushion of this type can then be carried out even if the cushion cover is slightly damaged.

It is particularly preferable for the sensor element not to be arranged directly on the sensor cushion, but rather to be connected to the sensor cushion via a hose or a flexible capillary. This has the advantage, inter alia, that the sensitive sensor element can be accommodated at an area (of the mattress) which is subjected to little or no mechanical load.

The advantageous evaluation of the absolute pressures on the sensor cushions and/or the relative pressures between a plurality of sensor cushions enables various data concerning the person on the mattress to be recorded. In particular, a combination of an absolute pressure measurement and a measurement of the relative pressure changes and the temporal profile thereof enables movements of a person on the mattress to be detected. In particular, the invention makes it possible to establish whether a significant change in position has actually taken place during a movement, for example from a position in which the person is lying on his side into a position in which he is lying on his back, or vice versa, or whether the movement was only, for example, a leg movement or an external manipulation of the bed or the mattress without a significant change in the bodily position of the person. This question is of importance if a mattress is to be used for preventing decubitus.

BRIEF DESCRIPTION OF THE DRAWINGS

Further details of the invention are explained in more detail below with reference to the exemplary embodiments illustrated in the drawing, in which:

FIG. 1 shows a side view of the basic structure of a mattress;

FIG. 2 shows a pressure sensor with sensor cushion and sensor element according to a first exemplary embodiment;

FIG. 3 shows a pressure sensor with sensor cushion and sensor element according to a second exemplary embodiment;

DETAILED DESCRIPTION OF THE PREFERRED EMBODIMENTS

Figure 4:
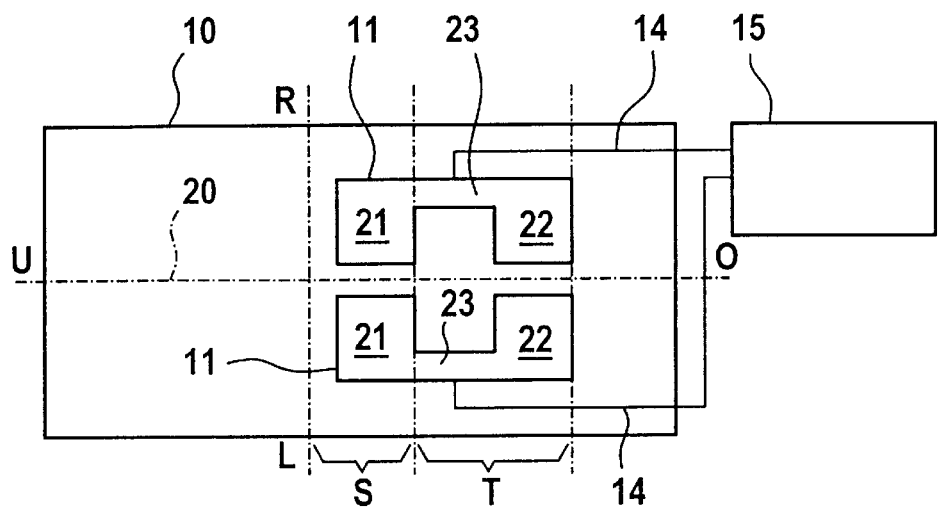
FIG. 4 shows the basic arrangement of two sensor cushions on a mattress in a view from above in accordance with a further exemplary embodiment.

FIG. 1 shows a mattress 10 with a sensor cushion 11 recessed on the top side of the mattress. The sensor cushion 11 is shaped in such a way that it fits into a correspondingly shaped recess in the mattress 10. The shape and the recess are designed in such a manner that the surface of the mattress does not exhibit any height discrepancies even in the region of the sensor cushion 11, that is to say the surface lies in a single plane.

The sensor cushion 11 covers a large area of the top side of the mattress 10. Based on the surface area of the top side of the mattress, it covers approximately 3% to 50%, preferably 5% to 25%, per sensor cushion 11.

A sensor element or pressure pick-up 12 is arranged on the sensor cushion 11. The sensor element or pressure pick-up 12 and sensor cushion 11 form a so-called pressure sensor 13. The pressure pick-up 12 is connected to an evaluation unit 15 via a measurement line 14. The evaluation unit 15 records and analyses the measurement data. In addition, the evaluation unit 15 performs suitable follow-up operations. These follow-up operations may in particular include activation of a control unit 16 which is bidirectionally connected to the evaluation unit 15 via a data line 17. Information or data is exchanged between the evaluation unit 15 and the control unit 16 via this data line 17.

In response to information input to the evaluation unit 15 via the data line 16, the control unit 16 can set a mattress core in motion. For this purpose, a control line 18 is provided leading from the control unit 17 to the mattress 10. The control line 18 may, for example, be an electric line for transmitting electric power, which in order to electrically drive electric movement components, in particular electric servomotors, are arranged inside or on the mattress. However, the control line may also be a hydraulic or pneumatic line, in which case the control unit 16 can pump a liquid or a gas, for example air, into the mattress 10.

These movements of the mattress 10 or the mattress core can be used to move and stimulate a bedridden patient. In this way, it is possible to prevent pressure sores. In particular, the control unit 16 and the members which are connected to the control line 18 can be used to change the position of maximum pressure on the person lying on the mattress 10. Furthermore, the zones of compressive load acting on a person lying down can be changed by vertical adjustment of the members. Finally, it is also possible for the hardness of the sensor cushions 11 filled with air or liquid to be varied as a function of control commands from the control unit 18, in order to relieve the pressure on the person.

FIG. 2 shows an enlarged perspective view of a sensor cushion 11. The sensor element or pressure pick-up 12 is also shown in an enlarged view. In this exemplary embodiment, this pressure pick-up is situated in the cover of the sensor cushion 11 and is connected to the evaluation unit 15 via the measurement line 14.

The sensor cushion 11 is preferably of cuboidal design. However, it may also be of different design or even not have any preferred shape. For example, it is also possible for the cover of the sensor cushion 11 to be made from a material of non-specific shape. A cushion of this nature can then be given a specific shape by a foam filling of defined shape. In this way, it is possible to use extremely simple means to arrange a sensor cushion 11 at any kind of recess inside a mattress 10. Designing the sensor cushion 11 in this way is also advantageous when the sensor cushion 11 is, for example, to be retrofitted inside a mattress 10. In this case, the mattress core or mattress filling can be removed in any desired way, and the cushion 11 can then be fitted accurately into this recess.

FIG. 3 shows a further variant of the sensor cushion 11 with a hose or flexible capillary 19 which connects the sensor element 12 to the sensor cushion 11. In this way, the sensor element 12 and the measurement lines 14 can be accommodated at a position which is remote from the cushion 11.

The sensor cushion 11 described can be used to detect the movement of a person lying on the mattress 10. In this case, a plurality of sensor cushions 11 are arranged in such a manner that they are partially or completely covered by the upper body of the patient. movements of the person cause pressure changes in the cushions 11. The resultant pressure is transferred via a medium—for example gaseous media such as air, or liquid media, such as water—to a pressure pick-up. Pressure patterns which are generated in this way are recorded by the pressure pick-ups and analysed, so that it is possible to draw conclusions as to whether the person has moved. For this purpose, the measurement data which has been recorded is combined in a calculation in the evaluation unit. To detect movement, in particular two, three, four or more sensor cushions 11 are provided. Both the absolute pressures from the sensor cushions and relative pressures between a plurality of sensor cushions are used in a combined calculation so that one or more movement signals are generated as a result.

However, it is also possible to obtain further signals from the physiology of the person, In particular, the sensor cushions 11 can also be used to detect heart sounds and muscle movements and the respiration of the person. For this purpose, even a single sensor cushion is sufficient, but the results become more accurate with more cushions. In particular, with a plurality of measurements from different sensor cushions it is possible to filter out or suppress by calculation any disturbances.

In addition, temperature sensors (not shown) may be provided on the top side of the mattress, in particular in the region of the sensor cushions 11. These additional temperature sensors also enable the position of the person to be determined, since the person emits heat to the mattress. As a result of both temperature values and pressure values being taken into account, the information content of the measurement is increased, and therefore so is the accuracy of the measured values. The temperature measurement provides in particular an additional plausibility criterion. In particular, the temporal profile of the pressures and temperature measurements makes it possible to draw further conclusions on the behavior of the person, as well as his vital parameters, such as respiration or heartbeat.

FIG. 4 shows a preferred embodiment of the mattress 10 with two sensor cushions 11 which are connected to the evaluation unit 15 via measurement lines 14. The arrangement illustrated in FIG. 4 corresponds to the arrangement shown in FIG. 1, with the mattress 10 viewed from above. The two sensor cushions 11 are on either side of the longitudinal axis 20 of the mattress, i.e. one sensor cushion is situated on the left-hand side L of the mattress, while the other sensor cushion 11 is situated on the right-hand side R of the mattress.

The sensor cushions 11 illustrated in FIG. 4 are each of U-shaped design. They each comprise three chambers, namely two outer chambers 21, 22 and one inner chamber 23 which connects the outer chambers 21, 22.

Furthermore, the sensor cushions 11 in FIG. 4 each extend over the region of both the sacrum S and the thorax T of the mattress, i.e. over those areas where the abdomen and the chest of a person lying on the mattress come to rest. This arrangement is suitable in particular for picking up movement data about the person and data about the direction of the movement, i.e. whether the person moves or turns towards the right-hand or left-hand side R or L, respectively, of the mattress. Furthermore, this arrangement of the sensor cushions is also particularly suitable for picking up vital parameters, since in particular the region of the thorax T is covered over a large area.

Figure 5:
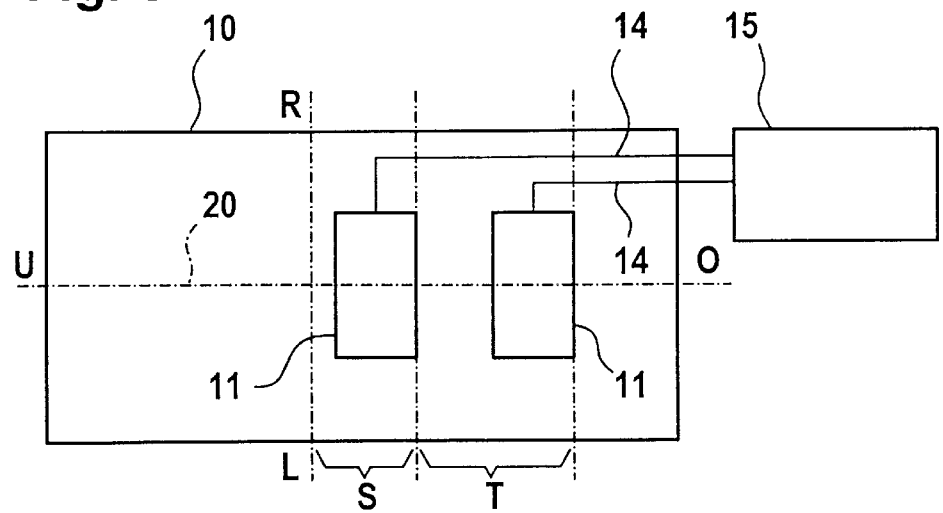
FIG. 5 shows the basic arrangement of two sensor cushions on a mattress, viewed from above in accordance with a further exemplary embodiment.

The arrangement shown in FIG. 5 makes it possible to pick up a direction of movement towards the head or foot end of the mattress 10, i.e. towards the upper end O of the mattress or the lower end U of the mattress, since two sensor cushions are arranged at different positions along the longitudinal axis 20 of the mattress. However, it is impossible to pick up the direction of movement towards the right-hand or left-hand side R or L, respectively, of the mattress. Otherwise, this arrangement corresponds to the arrangement shown in FIG. 4, in particular with regard to the measurement lines 14 and the evaluation unit 15.

Figure 6:
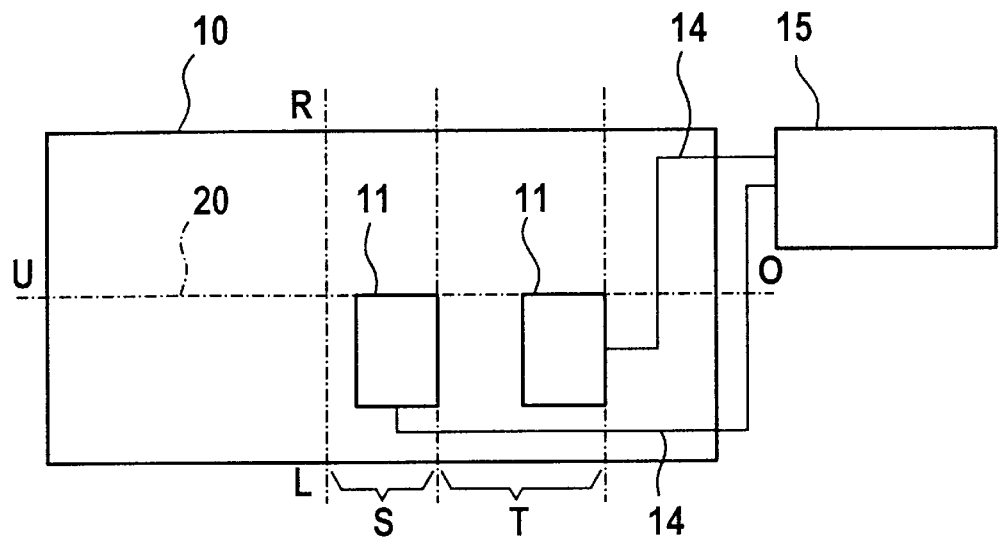
FIG. 6 shows the basic arrangement of two sensor cushions on a mattress, viewed from above in accordance with a further exemplary embodiment.

FIG. 6 shows a further exemplary embodiment of a mattress 10 with two sensor cushions 11, both sensor cushions 11 being arranged on one side of the longitudinal axis 20 of the mattress, that is to say on the same side. There is in each case one sensor cushion 11 in the region of the sacrum S and one in the region of the thorax T. Otherwise, the arrangement corresponds to FIGS. 4 and 5, in particular with regard to the measurement lines 14 and the evaluation unit 15. With this arrangement it is also possible to pick up the movement, in particular a movement to the right or the left and towards the head or foot end of the mattress, since the sensor cushions 11 in each case do not extend symmetrically with respect to the longitudinal axis 20 of the mattress, but rather are arranged on one side of the mattress.

Figure 7:
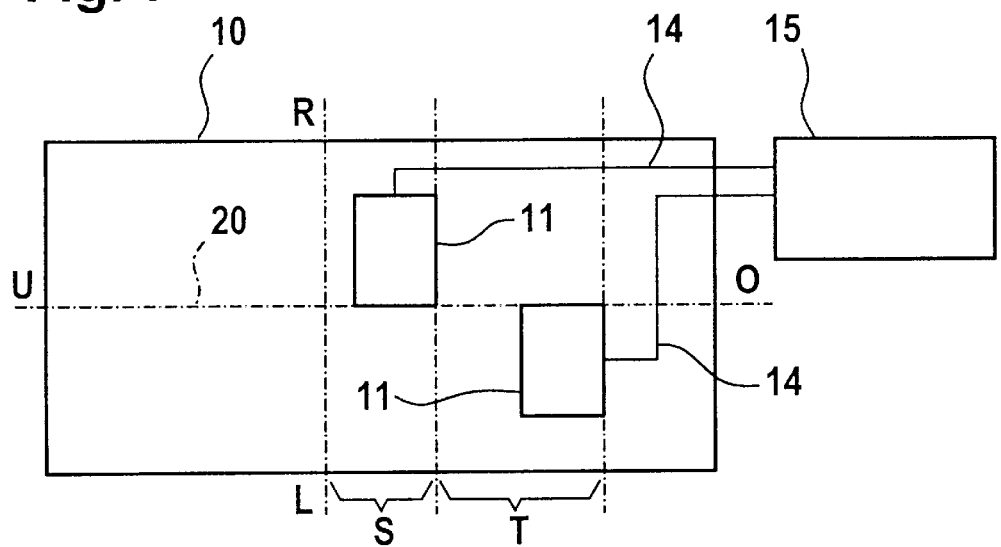
FIG. 7 shows the basic arrangement of two sensor cushions on a mattress, viewed from above in accordance with a further exemplary embodiment.

FIG. 7 shows a further exemplary embodiment with two sensor cushions, one of which is arranged in the region of the sacrum S on the right-hand side R of the mattress, and the other of which is arranged on the left-hand side L of the mattress, in the region of the thorax T. With this arrangement too, it is possible to pick up movements towards the right-hand side R of the mattress or towards the left-hand side L of the mattress and towards the upper end O of the mattress and towards the lower end U of the mattress. Furthermore, it is possible to measure vital parameters, in particular using the sensor cushion 11 arranged in the region of the thorax T. Otherwise, the device shown in FIG. 7 corresponds to FIGS. 4 to 6 in particular with regard to the measurement lines 14 and the evaluation unit 15.

Figure 8:
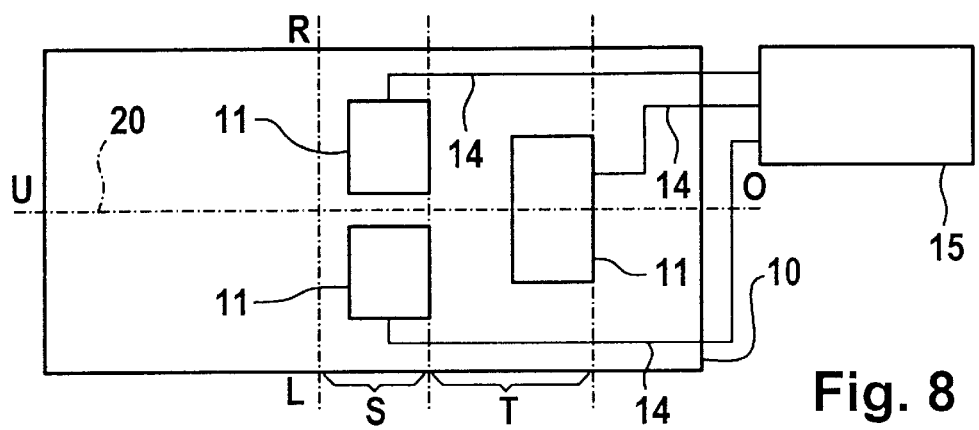
FIG. 8 shows the basic arrangement of three sensor cushions on a mattress, viewed from above in accordance with a further exemplary embodiment.

FIG. 8 shows an exemplary embodiment of a mattress 10 with three sensor cushions 11. Two of the sensor cushions 11 are situated in the region of the sacrum S. while the third sensor cushion is situated in the region of the thorax T. The two sensor cushions arranged in the region of the sacrum are arranged in such a manner that there is one sensor cushion on each side of the longitudinal axis 20 of the mattress, one sensor cushion 11 being situated on the left-hand side L of the mattress axmd the other sensor cushion 11 being situated on the right-hand side R of the mattress. The sensor cushion 11 situated at the thorax, on the other hand, extends over both the left-hand half of the mattress and the right-half of the mattress. The sensor cushion 11 which covers both the right-hand half of the mattress and the left-hand half of the mattress in the region of the thorax T is larger than each of the sensor cushions which are situated on only one side of the mattress in the region of the sacrum S. This arrangement also enables a movement of the person lying on the mattress 10, as well as the direction of this movement towards the right-hand side R or the left-hand side L of the mattress and towards the upper end O and towards the lower end U of the mattress to be detected. Otherwise, the arrangement corresponds to the arrangements shown in FIGS. 4 to 7, in particular with regard to the measurement lines 14 and the evaluation unit 15.

Figure 9:
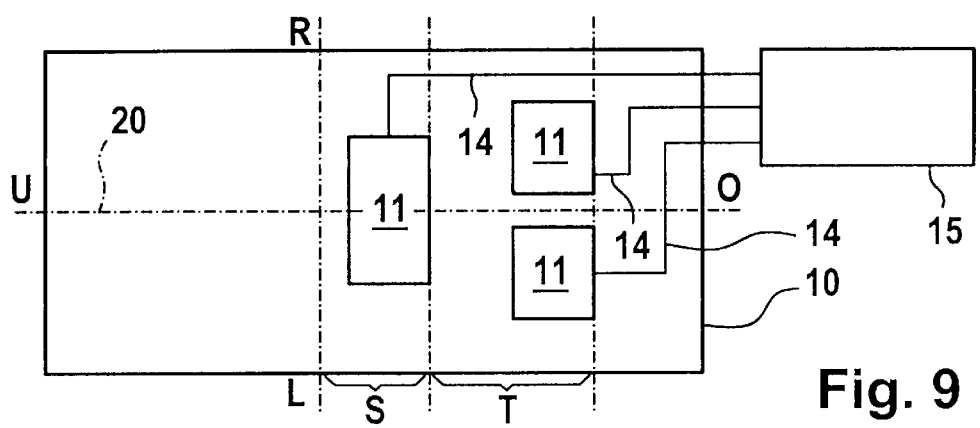
FIG. 9 shows the basic arrangement of three sensor cushions on a mattress, viewed from above in accordance with a further exemplary embodiment.

FIG. 9 shows a further arrangement with three sensor cushions 11 which is similar to the arrangement shown in FIG. 8. However, the sensor cushions 11 situated in the region of the thorax T and in the region of the sacrum S are switched over, so that in the region of the sacrum S there is only one sensor cushion 11 which is situated symmetrically on the right-hand side and left-hand side of the longitudinal axis 20 of the mattress. On the other hand, in the region of the thorax T there is in each case only one sensor cushion 11 on each side R and L of the mattress. Otherwise, the arrangement corresponds to the arrangements shown in FIGS. 4 to 8, in particular with regard to the measurement lines 14 and the evaluation unit 15.

Figure 10:
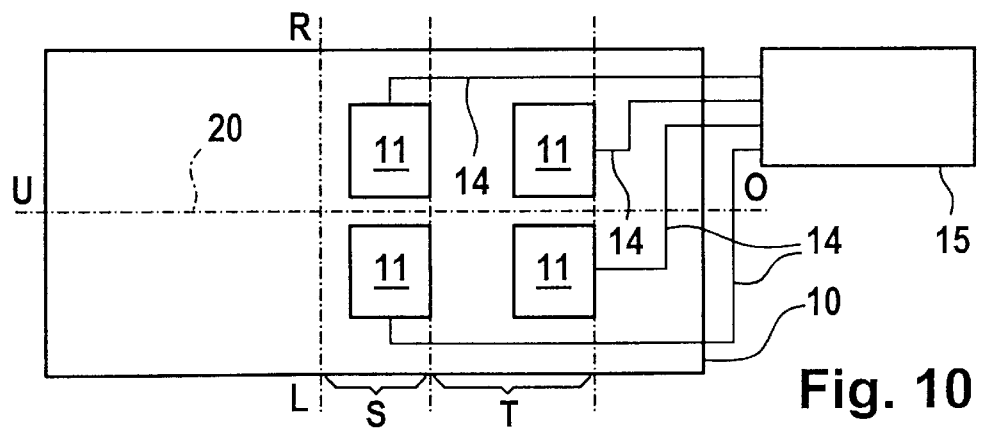
FIG. 10 shows the basic arrangement of four sensor cushions on a mattress, viewed from above in accordance with a further exemplary embodiment.

FIG. 10 shows an exemplary embodiment with four sensor cushions 11. In this arrangement, there are in each case two cushions in the region of the sacrum S and in the region of the thorax T. However, both in the region of the sacrum S and in the region of the thorax T there is in each case only one sensor cushion 11 on each side R or L of the mattress. This arrangement has the advantage that, in addition to the movement of the person and the direction of this movement towards the right-hand side R or left-hand side L of the mattress or towards the upper end O or towards the lower end U of the mattress, it can also determine the accurate centre of gravity of the person. Although in principle it is possible to determine a centre of gravity using three sensors arranged as shown in FIGS. 8 and 9, the determination of the centre of gravity is considerably more accurate with four sensor cushions 11.

Incidentally, the device shown in FIG. 10 can also be used to determine the vital parameters, as described above. The device shown in FIG. 10 otherwise corresponds to FIGS. 4 to 9, in particular with regard to the measurement lines 14 and the evaluation unit 15.

The sensor cushions according to the invention enable the measurement range of a pressure sensor 13 to be significantly increased, since a cushion 11 which is filled with a pressure-transmitting medium is connected to the pressure pick-up 12. However, this does not only increase the measurement area, but rather also increases the measurement range of a pressure pick-up, since the pressure pick-up can now record not only small pressures but also very high pressures. This is not possible with an isolated pressure pick-up without a connected sensor cushion.

As a result of the increase in measurement area, the pressure sensor according to the invention enables a mattress according to the invention to be provided with only a very small number of pressure sensors, in particular with only two, three or four pressure sensors, yet nevertheless to cover a large measurement area. A complicated, expensive structure, which is susceptible to faults, with a multiplicity of small, individual pressure pick-ups can thus be avoided.

The invention enables a mattress to be equipped with relatively large-area sensors, so that the parameters of movement which are sufficient for a wide range of applications in care or medical applications and the other vital parameters can be detected using the minimum possible number of sensors and with the minimum possible disruption to the quality of rest and the bed environment. For this purpose, the invention provides for sensor sizes, shape and arrangement to be selected in such a way that it is possible to sufficiently detect and qualify movements and measure the vital parameters which can be detected via pressure and movement sensors, namely the heart rate, respiration and any muscle tremors, using only two to five sensors. As an alternative or in addition to the sensor cushions described, it is also possible to use large-area semiconductor sensors.

Overall, the invention makes it possible to determine any movement of a person on a bed, it being possible to establish the extent of the movement. The proposed sensors also make it possible to determine whether a movement means a relevant change in position of the person, for example turning onto his side or turning over, or whether it is simply a "twitch". For this purpose, the values, in particular the change in shape or deformation of the sensors, are in particular measured continuously. In this case, it is possible, for example, to measure a pressure inside a sensor cushion or, for example, to derive another measurement signal, as for example with piezoelectric or other elements.

The small number of sensors are of large-area design and are arranged in a specific three-dimensional arrangement in or on the mattress or its sprung support. In particular, the sensors are arranged asymmetrically, so that it is possible to determine not only where the person is lying in the bed, but also how the person is lying, i.e. on his back, on his side or on his stomach, or the like. However, a symmetrical arrangement of the sensors is also possible.

Arranging at least one sensor in the region of the thorax makes it possible to measure dynamic values from the person, in particular his heartbeat and respiration. The continuous measurement and in particular ongoing recording of the measured values makes it possible to produce a record of how the person is lying. In this way, it is possible to monitor whether or not a person requiring care or a patient has been regularly turned by a nurse. This is advantageous in particular with regard to quality control in care homes and hospitals, since the lack of staff available in this sector means that care measures are ever more frequently not being carried out to the desired quality.

In addition or as an alternative to the sensor cushions described, sensors are arranged on or in the sprung support supporting the mattress, in particular on or in resilient bearing plates of a base for the mattress. These sensors have, for example, wire strain gauges. In this case, the movements of the person on the mattress are transmitted over a large area from the mattress to the bearing plates of the sprung support, which are preferably situated at certain points beneath the mattress. The deformation to the supporting plates or sprung support which occurs is then transmitted to the fitted wire strain gauges, which supply a change in measured value which is proportional to this deformation.

Overall, the particular arrangement of the sensors at only selected areas on a mattress or its sprung support, which are associated with particular areas of the body of a person on the mattress, in particular in the region of the thorax or in the region of the sacrum of this person, leads to the acquisition of measured values which provides very informative data on the way in which the person is lying and therefore the way in which care measures are being carried out.

What is claimed is:

1. An apparatus for measuring values to determine movements of a person lying on a mattress (10), comprising two pressure sensors (13) cooperating with the mattress (10), each pressure sensor (13) comprising a flat sensor cushion (11) filled with a fluid medium, wherein pressure exerted on the pressure sensors (13) by the person lying on the mattress (10) is transmitted via the fluid medium to a sensor element (12) associated with each sensor pad, wherein a first sensor cushion is arranged in the sacral (S) region of the person lying on the mattress and a second sensor cushion is arranged in the thorax (T) region of the person lying on the mattress, and both sensor cushions (11) are arranged substantially to one side of a longitudinal axis (20) of the mattress.

2. The apparatus according to claim 1, wherein at least one sensor has a wire strain gauge and at least one sensor is designed to measure a change in its shape.

3. The apparatus according to claim 1, wherein the sensors proximal to the thorax (T) region measure at least one value selected from the group consisting of the heartbeat, respiration, and physical position of the person lying on the mattress (10) and the sensors proximal to the sacral (S) region detect physical position of the person lying on the mattress (10).

4. Device according to claim 1, wherein the fluid medium is selected from the group consisting of gaseous and liquid mediums, and wherein each sensor cushion (11) is located proximal to a lying surface of the mattress (10).

5. The apparatus according to claim 1, further comprising an evaluation unit (15) for evaluating the measured values, wherein the sensors are connected to the evaluation unit (15).

6. The apparatus according to claim 1, wherein at least one sensor cushion (11) is of U-shaped design and has three chambers (21, 22, 23), namely two outer chambers (21, 22) and one inner chamber (23) which connects the two outer chambers (21, 22), wherein the inner chamber (23) is smaller that each of the outer chambers (21, 22).

7. An apparatus for measuring values to determine movements of a person lying on a mattress (10) comprising two pressure sensors (13) cooperating with the mattress (10), each pressure sensor (13) comprising a flat sensor cushion (11) filled with a fluid medium, wherein pressure exerted on the pressure sensors (13) by the person lying on the mattress (10) is transmitted via the fluid medium to a sensor element (12) associated with each sensor pad, wherein a first sensor cushion is arranged in the sacral (S) region of the person lying on the mattress and a second sensor cushion is arranged in the thorax (T) region of the person lying on the mattress, and one sensor cushion (11) is arranged to the right of a longitudinal axis (20) of the mattress and the other sensor cushion (11) is arranged to the left of the longitudinal axis (20) of the mattress.

8. The apparatus according to claim 7, wherein at least one sensor has a wire strain gauge and at least one sensor is designed to measure a change in its shape.

9. The apparatus according to claim 7, wherein the sensors proximal to the thorax (T) region measure at least ore value selected from the group consisting of the heartbeat, respiration, and physical position of the person lying on the mattress (10) and the sensors proximal to the sacral (S) region detect physical position of the person lying on the mattress (10).

10. Device according to claim 7, wherein the fluid medium is selected from the group consisting of gaseous and liquid mediums, and wherein each sensor cushion (11) is located proximal to a lying surface of the mattress (10).

11. The apparatus according to claim 7, further comprising an evaluation unit (15) for evaluating the measured values, wherein the sensors are connected to the evaluation unit (15).

12. The apparatus according to claim 7, wherein at least one sensor cushion (11) is of U-shaped design and has three chambers (21, 22, 23), namely two outer chambers (21, 22) and one inner chamber (23) which connects the two outer chambers (21, 22), wherein the inner chamber (23) is smaller that each of the outer chambers (21, 22).

13. An apparatus for measuring values used to determine movements of a person lying on a mattress (10), comprising two pressure sensors (13) cooperating with the mattress (10), each pressure sensor (13) comprising a flat sensor cushion (11) filled with a fluid medium, wherein pressure exerted on the pressure sensors (13) by the person lying on the mattress (10) is transmitted via the fluid medium to a sensor element (12) associated with each sensor pad, wherein both sensor cushions are arranged in the sacral (S) region of the person lying on the mattress, and both sensor cushions (11) are arranged substantially symmetrically with respect to a longitudinal axis (20) of the mattress.

14. The apparatus according to claim 13, wherein at least one sensor has a wire strain gauge and at least one sensor is designed to measure a change in its shape.

15. The apparatus according to claim 13, wherein the sensors proximal to the thorax (T) region measure at least one value selected from the group consisting of the heartbeat, respiration, and physical position of the person lying on the mattress (10) and the sensors proximal to the sacral (S) region detect physical position of the person lying on the mattress (10).

16. Device according to claim 13, wherein the fluid medium is selected from the group consisting of gaseous and liquid mediums, and wherein each sensor cushion (11) is located proximal to a lying surface of the mattress (10).

17. The apparatus according to claim 13, further comprising an evaluation unit (15) for evaluating the measured values, wherein the sensors are connected to the evaluation unit (15).

18. The apparatus according to claim 13, wherein at least one sensor cushion (11) is of U-shaped design and has three chambers (21, 22, 23), namely two outer chambers (21, 22) and one inner chamber (23) which connects the two outer chambers (21, 22), wherein the inner chamber (23) is smaller that each of the outer chambers (21, 22).

19. An apparatus for measuring values used to determine movements of a person lying on a mattress (10), comprising two pressure sensors (13) cooperating with the mattress (10), each pressure sensor (13) comprising a flat sensor cushion (11) filled with a fluid medium, wherein pressure exerted on the pressure sensors (13) by the person lying on the mattress (10) is transmitted via the fluid medium to a sensor element (12) associated with each sensor pad, wherein both sensor cushions are arranged in the thorax (T) region of the person lying on the mattress, and both sensor cushions (11) are arranged substantially symmetrically with respect to a longitudinal axis (20) of the mattress.

20. The apparatus according to claim 19, wherein at least one sensor has a wire strain gauge and at least one sensor is designed to measure a change in its shape.

21. The apparatus according to claim 19, wherein the sensors proximal to the thorax (T) region measure at least one value selected from the group consisting of the heartbeat, respiration, and physical position of the person lying on the mattress (10) and the sensors proximal to the sacral (S) region detect physical position of the person lying on the mattress (10).

22. Device according to claim 19, wherein the fluid medium is selected from the group consisting of gaseous and liquid mediums, and wherein each sensor cushion (11) is located proximal to a lying surface of the mattress (10).

23. The apparatus according to claim 19, further comprising an evaluation unit (15) for evaluating the measured values, wherein the sensors are connected to the evaluation unit (15).

24. The apparatus according to claim 19, wherein at least one sensor cushion (11) is of U-shaped design and has three chambers (21, 22, 23), namely two outer chambers (21, 22) and one inner chamber (23) which connects the two outer chambers (21, 22), wherein the inner chamber (23) is smaller that each of the outer chambers (21, 22).

25. An apparatus for measuring values used to determine movements of a person lying on a mattress (10), comprising three pressure sensors (13) cooperating with the mattress (10), each pressure sensor (13) comprising a flat sensor cushion (11) filled with a fluid medium, wherein pressure exerted on the pressure sensors (13) by the person lying on the mattress (10) is transmitted via the fluid medium to a sensor element (12) associated with each sensor pad, wherein two sensor cushions are arranged in the sacral (S) region of the person lying on the mattress and the third sensor cushion is arranged in the thorax (T) region of the person lying on the mattress.

26. The apparatus according to claim 25, wherein at least one sensor has a wire strain gauge and at least one sensor is designed to measure a change in its shape.

27. The apparatus according to claim 25, wherein the sensors proximal to the thorax (T) region measure at least one value selected from the group consisting of the heartbeat, respiration, and physical position of the person lying on the mattress (10) and the sensors proximal to the sacral (S) region detect physical position of the person lying on the mattress (10).

28. Device according to claim 25, wherein the fluid medium is selected from the group consisting of gaseous and liquid mediums, and wherein each sensor cushion (11) is located proximal to a lying surface of the mattress (10).

29. The apparatus according to claim 25, further comprising an evaluation unit (15) for evaluating the measured values, wherein the sensors are connected to the evaluation unit (15).

30. The apparatus according to claim 25, wherein at least one sensor cushion (11) is of U-shaped design and has three chambers (21, 22, 23), namely two outer chambers (21, 22) and one inner chamber (23) which connects the two outer chambers (21, 22), wherein the inner chamber (23) is smaller that each of the outer chambers (21, 22).

31. An apparatus for measuring values used to determine movements of a person lying on a mattress (10), comprising four pressure sensors (13) cooperating with the mattress (10), each pressure sensor (13) comprising a flat sensor cushion (11) filled with a fluid medium, wherein pressure exerted on the pressure sensors (13) by the person lying on the mattress (10) is transmitted via the fluid medium to a sensor element (12) associated with each sensor pad, two sensor cushions are arranged in the sacral (S) region of the Person lying on the mattress and two sensor cushions are arranged in the thorax (T) region of the person lying on the mattress, with all four sensor cushions being arranged symmetrically with respect to and at a distance from a longitudinal axis (20) of the mattress and at least one sensor has a wire strain gauge and at least one sensor is designed to measure a change in its shape.

32. The apparatus according to claim 31, wherein the sensors proximal to the thorax (T) region measure at least one value selected from the group consisting of the heartbeat, respiration, and physical position of the person lying on the mattress (10) and the sensors proximal to the sacral (S) region detect physical position of the person lying on the mattress (10).

33. Device according to claim 31, wherein the fluid medium is selected from the group consisting of gaseous and liquid mediums, and wherein each sensor cushion (11) is located proximal to a lying surface of the mattress (10).

34. The apparatus according to claim 31, further comprising an evaluation unit (15) for evaluating the measured values, wherein the sensors are connected to the evaluation unit (15).

35. An apparatus for measuring values used to determine movements of a person lying on a mattress (10), comprising four pressure sensors (13) cooperating with the mattress (10), each pressure sensor (13) comprising a flat sensor cushion (11) filled with a fluid medium, wherein pressure exerted on the pressure sensors (13) by the person lying on the mattress (10) is transmitted via the fluid medium to a sensor element (12) associated with each sensor pad two sensor cushions are arranged in the sacral (S) region of the person lying on the mattress and two sensor cushions are arranged in the thorax (T) region of the person lying on the mattress, with all four sensor cushions being arranged symmetrically with respect to and at a distance from a longitudinal axis (20) of the mattress and at least one sensor cushion (11) is of U-shaped design and has three chambers (21, 22, 23), namely two outer chambers (21, 22) and one inner chamber (23) which connects the two outer chambers (21, 22), wherein the inner chamber (23) is smaller that each of the outer chambers (21, 22).

* * * * *